United States Patent [19]

Boykin et al.

[11] Patent Number: 5,360,406
[45] Date of Patent: Nov. 1, 1994

[54] STYLET FOR RETROGRADE CORONARY SINUS CANNULA

[75] Inventors: Christopher M. Boykin, Saline; Thomas T. Vaalburg, Ann Arbor, both of Mich.

[73] Assignee: Minnesota Mining and Manufacturing Company, St. Paul, Minn.

[21] Appl. No.: 88,257

[22] Filed: Jul. 7, 1993

Related U.S. Application Data

[63] Continuation-in-part of Ser. No. 979,010, Nov. 19, 1992.

[51] Int. Cl.⁵ ................... A61M 5/178; A61M 25/00
[52] U.S. Cl. ...................................... 604/170; 604/282
[58] Field of Search ............... 604/61, 170, 264, 267, 604/282; 606/184, 185, 191; 128/772

[56] References Cited

U.S. PATENT DOCUMENTS

| Re. 32,306 | 12/1986 | Waters | 604/165 |
|---|---|---|---|
| 37,023 | 11/1862 | Woolley . | |
| D. 254,270 | 2/1980 | Ziegler | D24/23 |
| D. 309,014 | 7/1990 | Akerfeldt | D24/25 |
| D. 335,705 | 5/1993 | Buckberg et al. | D24/112 |
| 2,164,926 | 7/1939 | Kleine . | |
| 2,393,003 | 1/1946 | Smith . | |
| 2,541,402 | 2/1951 | Caine . | |
| 2,571,207 | 10/1951 | Cox | 604/267 |
| 2,955,592 | 10/1960 | MacLean . | |
| 3,419,010 | 12/1968 | Williamson . | |
| 3,459,188 | 8/1969 | Roberts . | |
| 3,469,580 | 9/1969 | Huddy . | |
| 3,521,620 | 7/1970 | Cook . | |
| 3,547,119 | 12/1970 | Hall et al. . | |
| 3,628,524 | 12/1971 | Jamshidi | 606/184 X |
| 3,630,198 | 12/1971 | Henkin . | |
| 3,653,388 | 4/1972 | Tenckhoff . | |
| 3,698,396 | 10/1972 | Katerndahl et al. . | |
| 3,726,269 | 4/1973 | Webster, Jr. . | |
| 3,757,768 | 9/1973 | Kline . | |
| 3,766,916 | 10/1973 | Moorehead et al. . | |
| 3,782,381 | 1/1974 | Winnie . | |
| 3,802,440 | 4/1974 | Salem et al. | 128/772 X |
| 3,809,081 | 5/1974 | Loveless . | |
| 3,845,473 | 12/1974 | Matsuo | 128/8 |
| 3,867,945 | 2/1975 | Long . | |
| 3,923,066 | 12/1975 | Francisoud et al. | 604/170 |
| 3,948,270 | 4/1976 | Hasson | 604/170 X |

(List continued on next page.)

FOREIGN PATENT DOCUMENTS

| 0141006 | 5/1985 | European Pat. Off. . |
|---|---|---|
| 434028 | 1/1912 | France . |
| WO92/08510 | 5/1992 | WIPO . |

OTHER PUBLICATIONS

Pp. 12–14 from a price listing of Research Medical, Inc. for Retroplegia Retrograde Cardioplegia, undated.
Brochure entitled "Retroplegia with Textured Balloon" (2 pages) from Research Medical, Inc., undated.
Brochure entitled "Retroplegia II–Coronary Sinus Cardioplegia Cannula with Retractaguard–Anti-retraction (List continued on next page.)

Primary Examiner—John D. Yasko
Assistant Examiner—Adam J. Cermak
Attorney, Agent, or Firm—Gary L. Griswold; Walter N. Kirn; Stephen W. Bauer

[57] ABSTRACT

A stylet for guiding a retrograde coronary sinus cannula into a coronary sinus. The stylet comprises an elongate shaft having proximal and distal ends, and a handle at the proximal end of the shaft. The handle includes a lever extending laterally outwardly relative to the shaft. The lever has a notch for receiving a digit of the user generally adjacent the shaft to define a fulcrum generally adjacent the shaft, with the lever extending laterally outwardly beyond the notch to facilitate rotation of the stylet around the longitudinal axis of the shaft. Also disclosed are first and second opposed indentations in a cylindrical portion of the handle.

31 Claims, 4 Drawing Sheets

U.S. PATENT DOCUMENTS

| | | | |
|---|---|---|---|
| 3,957,055 | 5/1976 | Linder et al. | |
| 3,995,623 | 12/1976 | Blake et al. | |
| 4,068,659 | 1/1978 | Moorehead | |
| 4,068,660 | 1/1978 | Beck | |
| 4,137,916 | 2/1979 | Killman et al. | 604/170 |
| 4,185,639 | 1/1980 | Linder | 128/200.26 |
| 4,273,131 | 6/1981 | Olsen | |
| 4,351,334 | 9/1982 | Inglefield, Jr. | |
| 4,351,341 | 9/1982 | Goldberg et al. | |
| 4,400,168 | 8/1983 | Buschel et al. | 604/48 |
| 4,417,886 | 11/1983 | Frankhouser et al. | 604/53 |
| 4,456,017 | 6/1984 | Miles | 128/772 |
| 4,458,677 | 7/1984 | McCorkie, Jr. | 128/786 |
| 4,459,977 | 7/1984 | Pizon et al. | |
| 4,469,109 | 9/1984 | Mehl | 128/753 |
| 4,504,268 | 3/1985 | Herlitze | 604/170 |
| 4,529,400 | 7/1985 | Scholten | 604/95 |
| 4,545,390 | 10/1985 | Leary | 128/772 |
| 4,559,041 | 12/1985 | Razi | 604/157 |
| 4,581,019 | 4/1986 | Curelaru et al. | 604/164 |
| 4,600,014 | 7/1986 | Beraha | 128/754 |
| 4,619,274 | 10/1986 | Morrison | 128/772 |
| 4,630,616 | 12/1986 | Tretinyak | 128/753 |
| 4,632,668 | 12/1986 | Wilson, Jr. et al. | 604/8 |
| 4,637,388 | 1/1987 | Melendy | 128/207.14 |
| 4,655,226 | 4/1987 | Lee | 128/754 |
| 4,676,249 | 6/1987 | Arenas et al. | 128/657 |
| 4,689,041 | 8/1987 | Corday et al. | 604/53 |
| 4,699,138 | 10/1987 | Behrstock | 128/207.16 |
| 4,699,140 | 10/1987 | Holmes et al. | 128/303 |
| 4,702,261 | 10/1987 | Cornell et al. | 128/754 |
| 4,713,049 | 12/1987 | Carter | 604/8 |
| 4,726,369 | 2/1988 | Mar | 128/303 |
| 4,743,265 | 5/1988 | Whitehouse et al. | 604/161 |
| 4,787,884 | 11/1988 | Goldberg | 604/8 |
| 4,790,825 | 12/1988 | Bernstein et al. | 604/170 |
| 4,793,363 | 12/1988 | Ambermann et al. | 128/754 |
| 4,808,158 | 2/1989 | Kreuzer et al. | 604/49 |
| 4,808,168 | 2/1989 | Warring | 604/158 |
| 4,834,709 | 5/1989 | Banning et al. | 604/170 |
| 4,838,282 | 6/1989 | Strasser | 128/754 |
| 4,846,186 | 7/1989 | Box et al. | 128/657 |
| 4,863,430 | 9/1989 | Klyce et al. | 604/164 |
| 4,863,439 | 9/1989 | Sanderson | 604/264 |
| 4,886,067 | 12/1989 | Palermo | 128/657 |
| 4,888,000 | 12/1989 | McQuilkin et al. | 604/164 |
| 4,923,061 | 5/1990 | Trombley, III | 206/364 |
| 4,925,445 | 5/1990 | Sakamoto et al. | 604/95 |
| 4,927,412 | 5/1990 | Menasche | 604/96 |
| 4,955,872 | 9/1990 | Callaway | 604/273 |
| 4,976,688 | 12/1990 | Rosenblum | 604/95 |
| 5,001,825 | 3/1991 | Halpern | 29/456 |
| 5,007,434 | 4/1991 | Doyle et al. | 128/772 |
| 5,021,045 | 6/1991 | Buckberg et al. | 604/53 |
| 5,047,018 | 9/1991 | Gay et al. | 604/164 |
| 5,103,296 | 5/1991 | Buckberg et al. | 604/44 |
| 5,108,413 | 4/1992 | Moyers | 606/191 |
| 5,131,406 | 7/1992 | Kaltenbach | 128/772 |
| 5,161,534 | 11/1992 | Berthiaume | 128/657 |
| 5,163,912 | 11/1992 | Gay et al. | 604/164 |
| 5,169,397 | 12/1992 | Sakashita et al. | 606/27 |
| 5,176,647 | 1/1993 | Knoepfler | 604/158 |
| 5,188,630 | 2/1993 | Christoudias | 604/1 |
| 5,203,866 | 4/1993 | Islam | 606/186 |
| 5,226,427 | 7/1993 | Buckberg et al. | 128/772 |

OTHER PUBLICATIONS

Lumen" (2 pages) from Research Medical, Inc., undated.

Brochure entitled "Looking for a Retrograde Cardioplegia Cannula with a Manually-Inflated, Textured Silicone Balloon?" (1 page) from Research Medical, Inc., undated.

Brochure entitled "Directions for Use: Retrograde Coronary Sinus Perfusion Cannula with Auto-Inflating-/Deflating Retention Cuff and Introducer" of DLP, Inc. dated Aug. 22, 1990.

Brochure entitled "Vent Catheters" from Research Medical, Inc. (undated).

Brochure entitled "Instructions for Use: Retroplegia Cannula" of Research Medical, Inc. dated Nov. 25, 1991.

One page of a brochure entitled "Retroplegia Coronary Sinus Perfusion Cannula" of Research Medical, Inc. (undated).

(List continued on next page.)

OTHER PUBLICATIONS

C. R. Bard, Inc. reference, dated at patent office Jan. 26, 1940.

Brochure entitled "Sarns-Sterilized Disposable Instruments" dated Apr. 1984.

One page flyer entitled "DLP Introduces the New Retrograde Coronary Sinus Perfusion Cannula" (undated).

"Retrograde plumonary venous pressure measurement-Fact or artifact?"; Buckberg et al.; The Journal of Thoracic and Cardiovascular Surgery; vol. 59, No. 3, Mar. 1970, pp. 393–400.

Pp. 8 and 9 from Research Medical, Inc. Annual Report (undated).

Charles P. Bailey, M.D., et al., "Cardiac Surgery"; F. A. Davis Company, Philadelphia, Pa. 1960 pp. 50–52, 75–77.

Gumersindo Blanco, M.D. et al.; "A Direct Experimental Approach to the Aortic Valve II, Acute Retroperfusion of the Coronary Sinus", from the Department of Surgery and the Experimental Surgery Laboratory, School of Medicine, University of Puerto Rico, San Juan, Puerto Rico, Nov. 1955, pp. 171–177.

Edward P. Fitch, M.D., et al. "Obturators for Extracorporeal Circulation Cannulae"; J. Thoracic, Surg., vol. 37, No. 5, Sep. 2, 1958, pp. 663–664.

"Sarns Presterilized Atrial Vent Catheter and Left Vent Catheter", The Annals of Thoracic Surgery, vol. 19, No. 3, Mar. 1975.

"Catheter Fittings and Accessories", Cardiovascular Catheters and Accessories by United States Catheter and Instrument Corporation, New York, 1967–1968, p. 41.

"Mayo Coronary Perfusion Components (Balloon Style)" date and source unknown.

Brochure entitled "Catheters and Related Products", by American Cystoscope Makers, Inc. p. 2558, undated.

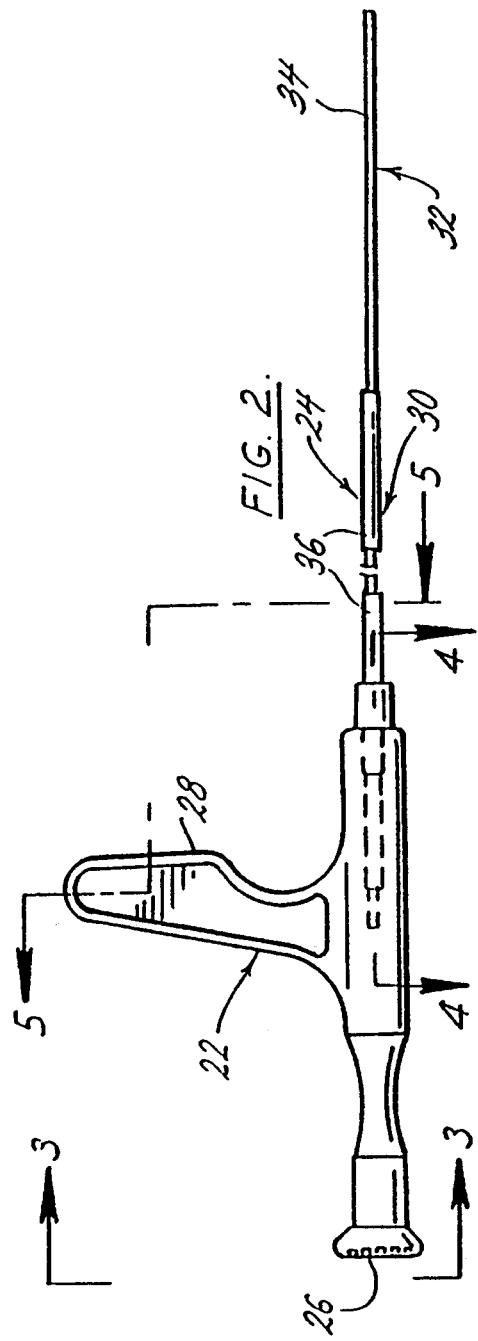

STYLET FOR RETROGRADE CORONARY SINUS CANNULA

This application is a continuation-in-part of co-pending U.S. patent application Ser. No. 07/979,010, filed Nov. 19, 1992, pending.

BACKGROUND AND SUMMARY OF THE INVENTION

This invention relates to a stylet for installing a retrograde coronary cannula.

Cardioplegia is a commonly used technique for protecting the heart during heart surgery in which a cooled cardioplegia solution, for example a potassium solution, is circulated through the heart. The cardioplegia solution stops the heart and reduces its temperature to minimize damage to the heart. Cardioplegia is often administered through the aorta in the antegrade direction, i.e., the direction of normal blood flow. However, there is increasing interest in administering cardioplegia in the retrograde direction, i.e., opposite the direction of normal blood flow. Retrograde administration of cardioplegia has been used in patients having critical coronary artery stenosis that would have made the antegrade administration of cardioplegia difficult and inefficient, and with patients suffering from aortal valve disease. Retrograde sinus catheters particularly adapted for the retrograde administration of cardioplegia is disclosed in U.S. patent application Ser. Nos. 07/874,589, filed Apr. 27, 1992, and 08/021,526, filed Feb. 23, 1993, incorporated herein by reference.

There are two principle techniques for installing a coronary cannula in the coronary sinus for the administration of cardioplegia. The first is known as the "open atrium" technique in which the right atrium of the heart is substantially opened with a large incision so that direct access is provided to the coronary sinus. A disadvantage of this technique is that it makes it more difficult to drain venous blood from the vena cava and to drain blood from the right atrium. An alternative is to use a "blind" procedure in which only a small incision is made to gain access to the right atrium and the coronary sinus. It can be very difficult to manipulate the coronary cannula, which is typically small and flexible, into the proper position in the coronary sinus through this small puncture.

Generally, the method of installing a coronary cannula according to this invention comprises providing a coronary cannula with a stylet extending through the lumen of the cannula. The stylet has a handle and a shaft that extends through the lumen with a stiff but flexible proximal portion, and a deformable distal portion. The shaft is sufficiently long that the deformable distal portion extends generally to the tip of the coronary cannula. The tip of the coronary cannula is then shaped by deforming the deformable distal portion of the stylet inside the lumen to facilitate its insertion through an incision in the right atrium and into the coronary sinus. The tip of the coronary cannula is then manipulated into the coronary sinus by steering the shaped tip by manipulating the handle. After the tip of the coronary cannula is in place, the cannula is anchored, for example by inflating a balloon at the tip of the cannula provided for that purpose, and the stylet can be drawn from the lumen of the coronary cannula.

Generally, the stylet apparatus for installing a coronary cannula according to this invention is adapted to fit inside the lumen of a coronary cannula to facilitate the installation of the cannula into the coronary sinus. The stylet comprises a handle, and a shaft extending from the handle and adapted to fit inside the lumen of the cannula. The shaft comprises a stiff but resilient proximal portion and a deformable distal portion that can be permanently deformed to a desired shape when inside the cannula to hold the tip of the cannula in a preselected shape to facilitate the insertion of the cannula into the coronary sinus. In the preferred embodiment the shaft comprises a malleable steel wire and a tube surrounding the proximal portion of the wire, stiffening the proximal portion of the shaft while leaving the distal portion of the wire uncovered. The deformable distal portion of the stylet is shorter than the stiffer proximal portion so that the deformability of the distal portion does not interfere with the steering of the tip, as described below. The distal portion of the stylet may be colored so that the surgeon can gauge the depth of penetration of the stylet and cannula in order to facilitate proper placement of the cannula.

The coronary cannula is preferably provided with the stylet already in the lumen, although they could be provided separately, and the stylet inserted into the lumen before the installation of the cannula. With the stylet inside the lumen of the coronary cannula, the tip of the coronary cannula can be configured to pass readily through an incision in the right atrium and into the coronary sinus. The malleable distal portion of the stylet holds the tip of the cannula in the desired preformed configuration, while the stiffer, flexible proximal portion of the stylet allows the cannula to flex and bend sufficiently as the tip of the cannula is manipulated into the coronary sinus.

The method of installing the coronary cannula and the stylet apparatus for installing the cannula allow the cannula to be quickly inserted into the coronary sinus for the prompt administration of cardioplegia solution. The stylet apparatus also helps the surgeon gauge the depth of the tip to facilitate proper placement. The method and apparatus provide for the accurate placement of the cannula, and hold the cannula in place until it is anchored, for example by inflating a balloon on the cannula.

These and other features and advantages will be in part apparent, and in part pointed out, hereinafter.

BRIEF DESCRIPTION OF THE DRAWINGS

FIG. 2 is a partial side elevation view of the stylet;

DETAILED DESCRIPTION OF THE PREFERRED EMBODIMENT

Figure 1:
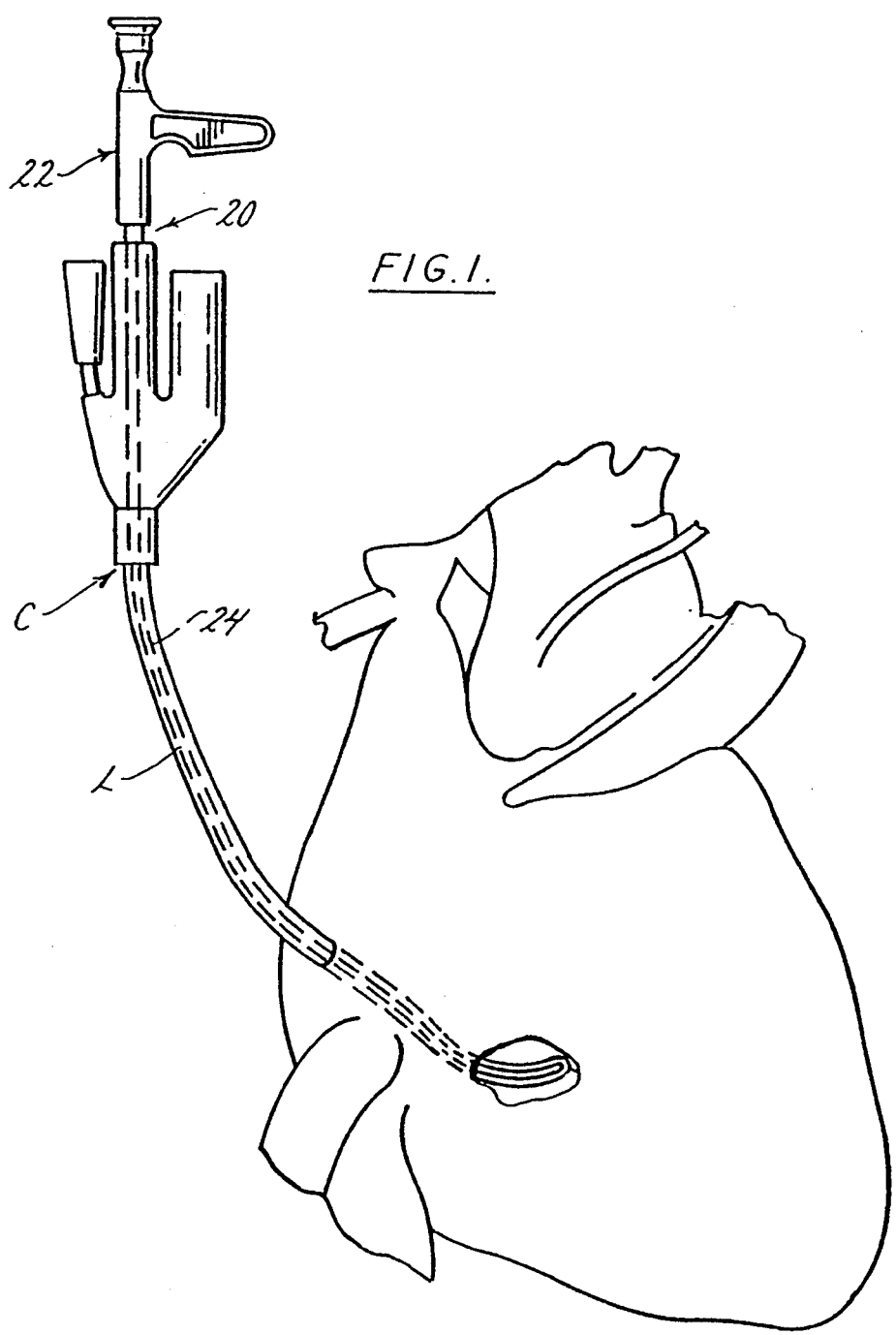
FIG. 1 is a view of a stylet constructed according to the principles of this invention, inserted in the lumen of a coronary cannula, shown as it would be used to manipulate the cannula into the coronary sinus.
Figure 4:
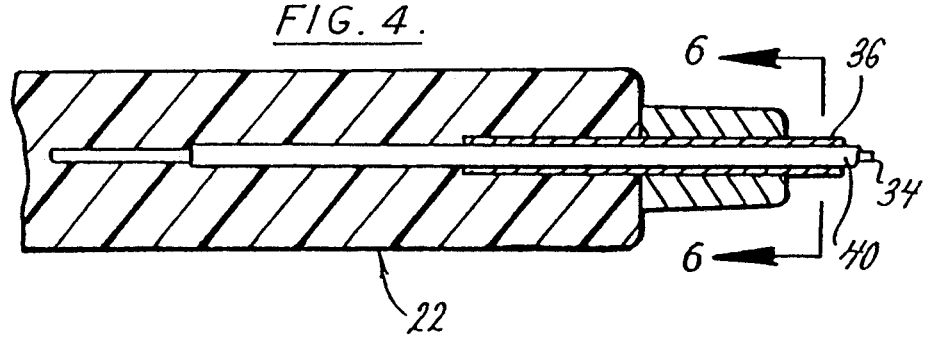
FIG. 4 is an enlarged partial longitudinal cross-sectional view taken along the plane of line 4—4 in FIG. 2.
Figure 5:
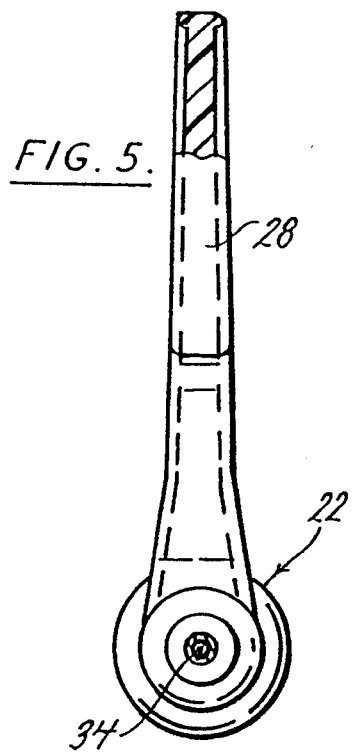
FIG. 5 is a vertical cross-sectional view of the stylet taken along line 5—5 in FIG. 2.
Figure 6:
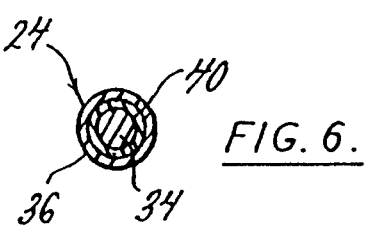
FIG. 6 is a vertical cross-sectional view of the stylet taken along the plane of line 6—6 in FIG. 4.
Figure 3:
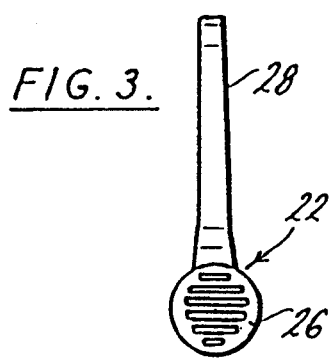
FIG. 3 is an end elevation view of the stylet taken along the plane of line 3—3 in FIG. 2.

A stylet apparatus for installing a coronary cannula in a coronary sinus is indicated generally at 20 in FIGS. 1 and 2. The stylet 20 comprises a handle 22 and a shaft 24 extending from the handle and adapted to fit inside the lumen L of a coronary cannula C. (See FIG. 1). In practice, the coronary cannula C can be provided premounted on the shaft 24 of a stylet 20, to facilitate the proper installation of the cannula C in the coronary sinus. Alternatively the stylet 20 and the cannula C could be provided separately. Preferred coronary sinus cannulae are disclosed in co-assigned U.S. patent application Ser. Nos. 07/874,589, filed Apr. 27, 1992, and 08/021,526, filed Feb. 23, 1993, both of which are hereby incorporated by reference.

The handle 22 of the stylet 20 preferably has a flat base 26, and a finger grip 28, so that the handle 22 can be grasped like a pistol, if desired. Of course some other style of handle could be provided. The handle 22 is preferably made from a molded plastic, such as ABS, although the handle 22 could be made from any other suitable material.

The shaft 24 of the stylet 20 preferably has a stiff but flexible proximal portion 30, and a shorter, malleable distal portion 32. As noted above, the shaft 24 is sized to fit in the lumen L of a coronary cannula C, and is sufficiently long that the distal end of the shaft 24 is closely adjacent to, but does not protrude from, the distal end of the coronary cannula C. (See FIG. 1). The distal portion 32 of the shaft 24 is sufficiently malleable that it can be shaped by hand to a configuration to facilitate the insertion of the cannula C and stylet 20 into the coronary sinus, yet the distal portion 32 is sufficiently stiff to substantially retain this shape as the tip of the cannula C and stylet 20 are manipulated into the coronary sinus. The proximal portion 30 of the shaft 24 is sufficiently stiff to allow the tip of the stylet 20 and cannula C to be steered by manipulating the handle 22. The proximal portion 30 is preferably not so rigid that it cannot be deformed by hand, for example to form a large radius arc in the proximal portion to facilitate installation of the cannula C. The relative lengths of the proximal and distal portions 30 and 32 are important to the steerability of the stylet 20 and cannula C. The distal portion 32 of the stylet 22 must be sufficiently long to hold the shape of the tip of the cannula mounted on the stylet 20. However, the distal portion 32 must be sufficiently short so that the cumulative effect of the flexibility of the distal portion 32 does not unduly interfere with the ability to steer the stylet 20 and cannula C. The distal portion 32 is preferably shorter than the proximal portion 30, and is preferably between about 2 and 3 inches (3.0 and 7.6 cm) long. The proximal portion 30 is preferably between about 9 and 10 inches (22.9 and 25.4 cm) long so that the overall length of the shaft 24 is about 12 inches (28.5 cm).

The shaft 24 preferably comprises a long, malleable wire 34 extending from the handle 22. The wire 34 is preferably made of a medical grade stainless steel, such as an SS 303 or SS 304 stainless steel, or other suitable material. The wire is dead soft (annealed), and of sufficient diameter that the wire can be easily shaped by hand into a desired configuration yet hold its shape while the cannula C and stylet 20 are manipulated into the coronary sinus. The wire preferably has a stiffness of between about 0.005 in/in and 0.025 in/in as determined by a standard Tenius-Olsen stiffness test with a 30 gram weight at a 0.75 inch deflection. See Federal Military Specification GGN-196, incorporated herein by reference, regarding Tenius-Olsen testing. The appropriate diameter may vary, depending on the size of the cannula C and the type of material used. For an SS 303 or 304 stainless steel a diameter of 0.040 inches (0.1016 cm) has been found to be satisfactory. The wire must be sufficiently stiff to retain its shape, but it must be sufficiently flexible to be comfortably manipulated by the surgeon by hand without damaging the cannula C. Also the wire must not be so stiff that it can puncture the tissue surrounding the coronary sinus.

An advantage of the malleable wire is that for a given tip sharpness, the greater the flexibility, the greater force required to penetrate a given structure, for example the wall of the coronary sinus. Penetration pressure can be measured using an Instron Stress Machine to push a test piece through a standard medium, such as a 3 mm or 5 mm thick polyethylene sheet. The inventors conducted such tests measuring the puncture pressure at 3 inches from the tip when formed in a "C" and 6 inches from the tip and found that the average puncture pressure for ten repetitions is significantly higher with inventors' compound stylet 20. This means that greater force can be applied to the inventors' stylet 20 without puncturing the heart tissue.

The proximal portion of the wire 34 (i.e., the portion adjacent the handle 22) is surrounded by a tubular sheath 36. The sheath 36 stiffens the proximal portion of the wire, forming the relatively stiff proximal portion 30 of the shaft 24. For a wire diameter of about 0.040 inches (0.1016 cm), the sheath 36 can be a 14 gauge stainless steel tube. Of course, with different wire diameters, different tube gauges can be used. The section of the wire 34 covered by the sheath 36 forms the stiff but flexible proximal portion 30. The compound construction with the wire 34 extending through the sheath 36 prevents the proximal portion 30 from kinking. The distal portion 32 of the wire 34 protruding from the sheath 36 forms the malleable distal portion 32 of the shaft. The compound construction of the shaft 24 is relatively simple and inexpensive to manufacture. The fact that the wire 34 extends the length of the shaft 24 reduces the risk that the distal portion 32 will break off or separate from the shaft 24.

The wire 34 preferably has a coating 40, which may be a nylon, such as "ZYTEL 408" nylon resin, or other suitable plastic. "ZYTEL 408 TM" is a trademark used in connection with a nylon resin available from E. I. Du Pont de Nemours & Company, Wilmington, Del. The coating 40 is preferably colored so that it is visible through the walls of the cannula C in which it is placed. The color of the coating 40 provides an indication of the depth of penetration of the tips of the cannula C and stylet 20 into the heart atrium, which helps to indicate when the tip of the cannula C is properly placed. At the point where the colored coating is no longer visible, the surgeon knows that the tips of the cannula C and stylet 20 are at a depth corresponding to the length of the proximal portion 30. This helps the surgeon to avoid inserting the cannula C past the coronary sinus, and possibly damaging the heart.

The entire stylet 20 is preferably coated with a silicone-based lubricant to facilitate the removal of the stylet 20 after the cannula C is properly placed in the coronary sinus. The lubricant allows the stylet 20 to be withdrawn without pulling the coronary cannula C from the heart. The coating 40 also facilitates the removal of the deformed distal portion 32 from the cannula C with a minimum of disruption.

Figure 7:
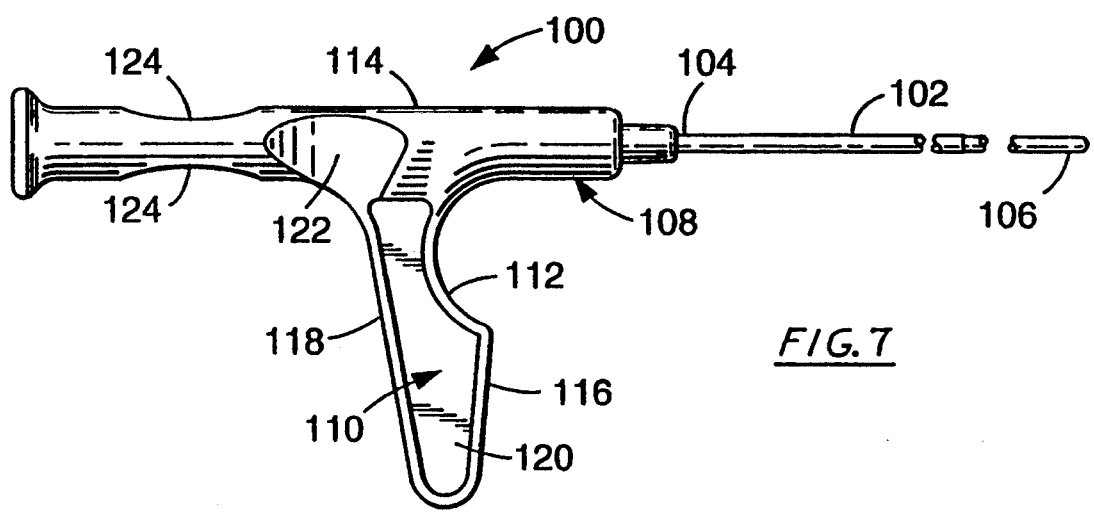
FIG. 7 is a side elevation view of a second embodiment of the stylet of the invention.
Figure 8:
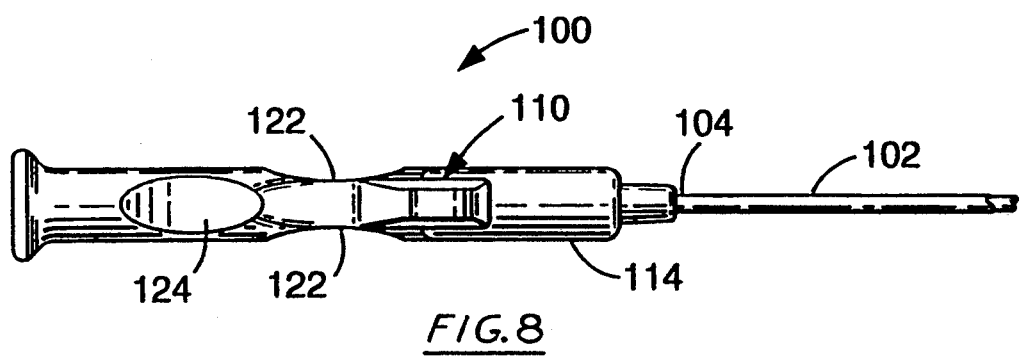
FIG. 8 is a bottom view of the stylet of FIG. 7.

FIGS. 7 and 8 illustrate a second embodiment of the stylet, herein 100, similar in many respects to the stylet 20 of FIGS. 1-6. The stylet 100 includes an elongate shaft 102, which is preferably similar to shaft 24 and which has proximal and distal ends 104 and 106. A handle 108 is provided at the proximal end 104 of the shaft 102. The handle 108 includes an elongate, generally cylindrical portion 114 extending proximally along the shaft 102, and a lever 110 extending laterally outwardly relative to the shaft 102. A notch 112 is provided in the lever 110 generally adjacent the cylindrical portion 114 of the handle 108. The notch 112 is adapted to receive a digit of the user to define a fulcrum generally adjacent the cylindrical portion 114. The lever 110 extends laterally outwardly beyond the notch 112 to facilitate manual rotation of the stylet 100 around the longitudinal axis of the shaft 102.

The lever 110 has front and rear edges 116 and 118 generally facing the distal and proximal directions, respectively, of the shaft 102, and opposite major surfaces, e.g., surface 120, extending between the front and rear edges 116 and 118. The notch 112 is formed in the front edge 116 of the lever 110.

Preferably, first and second pairs of opposed indentations 122 and 124 are provided in the cylindrical portion 114, with the second pair of opposed indentations 124 offset axially rearwardly relative to the first pair of indentations 122. The second pair of indentations 124 are also offset at approximately a right angle from the first pair of indentations 122. The first pair of indentations 122 are most preferably offset at approximately a right angle to the lever 110 so that the indentations 122 face in the same directions as the opposite major surfaces 120 of the lever 110. The first and second pairs of opposed indentations 122 and 124 are generally concave having a generally constant radius of curvature. The first and second pairs of opposed indentations 122 and 124 facilitate controlled manipulation, particularly rotation, of the stylet 100.

Most preferably the handle 108 is integrally molded of thermoplastic or thermosetting material. For example, the handle 108 may be integrally molded of acrylonitrile-butadiene-styrene resin ("ABS"). As used herein, "integrally molded" means molded in one continuous piece, without mechanical fastening or chemically adhering various parts together. Suitable thermosetting materials and alternative thermoplastic materials are well know in the art.

Figure 9:
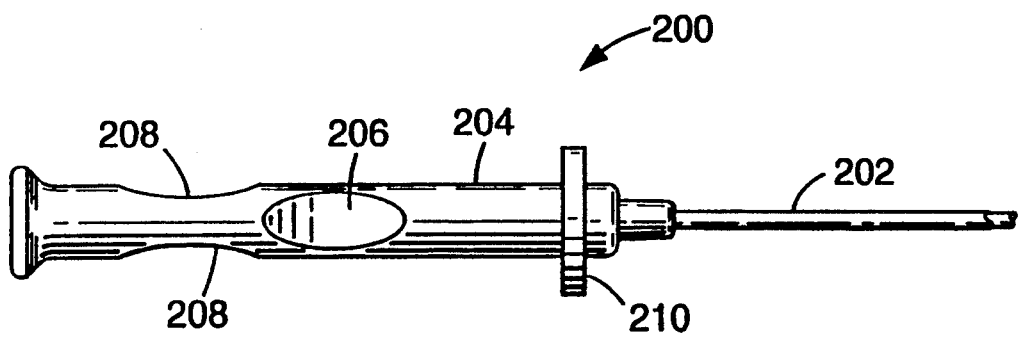
FIG. 9 is a side view of a third embodiment of the stylet of the invention.

FIG. 9 illustrates a third embodiment of the stylet, herein 200, similar in many respects to the stylets 20 and 200 of FIGS. 1-8. The stylet 200 includes an elongate shaft 202, which is preferably similar to shafts 24 and 102, and an elongate, generally cylindrical handle 204. The handle 204 of stylet 200 includes first and second pairs of opposed indentations 206 and 208 similar to indentations 122 and 124 of the stylet 100 of FIGS. 7 and 8.

The second pair of opposed indentations 208 are offset axially rearwardly relative to the first pair of indentations 206, and are also offset circumferentially at approximately a right angle from the first pair of indentations 206. The first and second pairs of opposed indentations 206 and 208 are generally concave having a generally constant radius of curvature. The first and second pairs of opposed indentations 206 and 208 facilitate controlled manipulation, particularly rotation, of the stylet 200.

The handle 204 optionally includes an enlarged annular rib 210. Most preferably the handle 204 is integrally molded of thermoplastic or thermosetting material. For example, the handle 204 may be integrally molded of acrylonitrile-butadiene-styrene resin ("ABS"). As used herein, "integrally molded" means molded in one continuous piece, without mechanical fastening or chemically adhering various parts together. OPERATION A coronary cannula C is preferably provided in a sterile package, already mounted on the shaft 24 of a stylet 20. The surgeon bends the tip of the cannula C, deforming the distal portion 32 of the shaft 24, to the desired configuration to facilitate the installation of the cannula C in the coronary sinus. The distal portion 32 deforms to hold the end of the coronary cannula C in the desired shape. An incision is made in the right atrium, and the coronary cannula C and stylet 20 are manipulated to bring the tip of the cannula C into the coronary sinus. The amount of colored coating 40 that is visible through the wall of the cannula C indicates to the surgeon the depth of the cannula tip in the heart. When the coronary cannula C is properly placed in the coronary sinus, it is anchored by means known in the art, for example, by inflating a balloon provided on the cannula C for that purpose. Once the coronary cannula C is firmly anchored, the stylet 20 is removed from the cannula C. The lubricant coating facilitates the removal of the stylet 20 from the coronary cannula C with a minimum of disruption to the cannula C.

As various changes could be made in the above constructions without departing from the scope of the invention, it is intended that all matter contained in the above description or shown in the accompanying drawings shall be interpreted as illustrative and not in a limiting sense.

We claim:

1. A stylet for guiding a retrograde coronary sinus cannula into a coronary sinus, the styler comprising:
    an elongate shaft having proximal and distal ends; and
    a handle at the proximal end of the shaft, the handle including a lever extending laterally outwardly relative to the shaft, the lever having a notch for receiving a digit of the user generally adjacent the shaft to define a fulcrum generally adjacent the shaft, the lever extending laterally outwardly beyond the notch to facilitate rotation of the stylet around the longitudinal axis of the shaft;
    the handle further comprising an elongate, generally cylindrical portion extending proximally along the shaft from the lever.

2. A stylet according to claim 1 wherein the lever has front and rear edges generally facing the distal and proximal ends, respectively, and opposite major surfaces extending between the front and rear edges.

3. A stylet according to claim 2 wherein the notch is formed by the front edge of the lever.

4. A stylet according to claim 3 wherein the handle is integrally molded of material selected from the group consisting of thermoplastic and thermosetting material.

5. A stylet according to claim 1 wherein the cylindrical portion has a first pair of opposed indentations.

6. A stylet according to claim 5 wherein the cylindrical portion has a second pair of opposed indentations offset axially relative to the first pair of opposed indentations, the second pair of opposed indentations also being offset from the first pair of opposed indentations by an approximately right angle along the cylindrical portion.

7. A stylet according to claim 6 wherein the first and second pairs of opposed indentations are generally concave having a generally constant radius of curvature.

8. A stylet according to claim 6 wherein the lever has a longitudinal axis defining a first lateral direction, the first pair of opposed indentations being offset along the cylindrical portion from the first lateral direction by an approximately right angle.

9. A stylet according to claim 8 wherein the second pair of indentations are offset axially rearwardly from the first pair of indentations.

10. A stylet according to claim 9 wherein the lever has front and rear edges generally facing the distal and proximal ends, respectively, and opposite major surfaces extending between the front and rear edges.

11. A stylet according to claim 10 wherein the notch is formed by the front edge of the lever.

12. A stylet according to claim 11 wherein the handle is integrally molded of material selected from the group consisting of thermoplastic and thermosetting material.

13. A stylet for guiding a retrograde coronary sinus cannula into a coronary sinus, the stylet comprising:
an elongate shaft having proximal and distal ends, the shaft comprising a stiff proximal portion and a deformable distal portion, shorter than the proximal portion, which when inside a coronary cannula can be deformed to hold a distal tip of the coronary cannula in a desired orientation to facilitate insertion of the cannula into the coronary sinus; and
a handle at the proximal end of the shaft, the handle including a lever extending laterally outwardly relative to the shaft, the lever having a notch for receiving a digit of the user generally adjacent the shaft to define a fulcrum generally adjacent the shaft, the lever extending laterally outwardly beyond the notch to facilitate rotation of the stylet around the longitudinal axis of the shaft.

14. A stylet according to claim 13 wherein the shaft includes a malleable wire forming the distal portion and extending in the proximal portion, the stiff proximal portion of the shaft including a sleeve surrounding the proximal portion of the wire, thereby stiffening the proximal portion of the shaft.

15. A stylet for guiding a retrograde coronary sinus cannula into a coronary sinus, the stylet comprising:
an elongate shaft having proximal and distal ends; and
a handle at the proximal end of the shaft, the handle being generally elongate and cylindrical extending co-axially with the shaft, the handle having first and second pairs of opposed indentations, the second pair of opposed indentations being offset axially relative to the first pair of opposed indentations, the second pair of opposed indentations also being offset from the first pair of opposed indentations by an approximately right angle along the cylindrical portion.

16. A stylet according to claim 15 wherein the first and second pairs of opposed indentations are generally concave having a generally constant radius of curvature.

17. A combination of a retrograde coronary sinus cannula for administering blood and/or cardioplegia to a patient's heart, and a stylet for guiding the retrograde coronary sinus cannula into a coronary sinus;
the cannula being generally elongate and having at least an infusion lumen for supplying cardioplegia and/or blood into the coronary sinus;
the stylet comprising:
an elongate shaft having proximal and distal ends, the elongate shaft being adapted to be inserted into the infusion lumen of the cannula; and
a handle at the proximal end of the shaft, the handle being generally elongate having a central longitudinal axis extending generally coaxially with the shaft, the handle having first and second pairs of opposed indentations, the second pair of opposed indentations being offset axially relative to the first pair of opposed indentations, the second pair of opposed indentations also being radially offset from the first pair of opposed indentations about the central longitudinal axis of the handle.

18. A combination according to claim 17 wherein the second pair of opposed indentations are radially offset from the first pair of opposed indentations by an approximately right angle.

19. A combination according to claim 18 wherein the handle is generally cylindrical.

20. A combination according to claim 19 wherein the first and second pairs of opposed indentations are generally concave having a generally constant radius of curvature.

21. A combination according to claim 20 wherein the handle is integrally molded of material selected from the group consisting of thermoplastic and thermosetting material.

22. A combination according to claim 17 wherein the first and second pairs of opposed indentations are generally concave having a generally constant radius of curvature.

23. A combination of a retrograde coronary sinus cannula for administering blood and/or cardioplegia to a patient's heart, and a stylet for guiding the retrograde coronary sinus cannula into a coronary sinus;
the cannula being generally elongate and having at least an infusion lumen for supplying cardioplegia and/or blood into the coronary sinus;
the stylet comprising:
an elongate shaft having proximal and distal ends, the elongate shaft being adapted to be inserted into the infusion lumen of the cannula; and
a handle at the proximal end of the shaft, the handle including a lever extending laterally outwardly relative to the shaft, the lever having a notch for receiving a digit of the user generally adjacent the shaft to define a fulcrum generally adjacent the shaft, the lever extending laterally outwardly beyond the notch to facilitate rotation of the stylet around the longitudinal axis of the shaft;
the lever has front and rear edges generally facing the distal and proximal ends, respectively, and opposite major surfaces extending between the front and rear edges, the notch being formed by the front edge of the lever.

24. A combination according to claim 23 wherein the handle of the stylet is integrally molded of material selected from the group consisting of thermoplastic and thermosetting material.

25. A combination of a retrograde coronary sinus cannula for administering blood and/or cardioplegia to a patient's heart, and a stylet for guiding the retrograde coronary sinus cannula into a coronary sinus;

the cannula being generally elongate and having at least an infusion lumen for supplying cardioplegia and/or blood into the coronary sinus;

the stylet comprising:

an elongate shaft having proximal and distal ends, the elongate shaft being adapted to be inserted into the infusion lumen of the cannula; and a handle at the proximal end of the shaft, the handle including a lever extending laterally outwardly relative to the shaft, the lever having a notch for receiving a digit of the user generally adjacent the shaft to define a fulcrum generally adjacent the shaft, the lever extending laterally outwardly beyond the notch to facilitate rotation of the stylet around the longitudinal axis of the shaft;

the handle of the stylet further comprising an elongate, generally cylindrical portion extending proximally along the shaft from the lever, the cylindrical portion having a first and second pairs of opposed indentations, the second pair of opposed indentations being offset axially relative to the first pair of opposed indentations, the second pair of opposed indentations also being offset from the first pair of opposed indentations by an approximately right angle along the cylindrical portion.

26. A combination according to claim 25 wherein the first and second pairs of opposed indentations are generally concave having a generally constant radius of curvature.

27. A combination according to claim 25 wherein the lever has a longitudinal axis defining a first lateral direction, the first pair of opposed indentations being offset along the cylindrical portion from the first lateral direction by an approximately right angle, the second pair of indentations being offset axially rearwardly from the first pair of indentations.

28. A combination according to claim 27 wherein the lever has front and rear edges generally facing the distal and proximal ends, respectively, and opposite major surfaces extending between the front and rear edges, the notch being formed by the front edge of the lever.

29. A combination according to claim 28 wherein the handle is integrally molded of material selected from the group consisting of thermoplastic and thermosetting material.

30. A combination according to claim 28 wherein the shaft comprises a stiff proximal portion and a deformable distal portion, shorter than the proximal portion, which when inside the coronary sinus cannula can be deformed to hold a distal tip of the coronary cannula in a desired orientation to facilitate insertion of the cannula into the coronary sinus.

31. A combination according to claim 30 wherein the shaft includes a malleable wire forming the distal portion and extending in the proximal portion, the stiff proximal portion of the shaft including a sleeve surrounding the proximal portion of the wire, thereby stiffening the proximal portion of the shaft.

* * * * *